United States Patent [19]
Caceci et al.

[11] Patent Number: 5,932,697
[45] Date of Patent: Aug. 3, 1999

[54] SYNTHETIC ANTIFREEZE PEPTIDE

[75] Inventors: Thomas Caceci; Thomas E. Toth, both of Blacksburg; Maria B. Szumanski, Roanoke, all of Va.

[73] Assignee: Virginia Tech Intellectual Properties, Inc., Blacksburg, Va.

[21] Appl. No.: 07/812,421

[22] Filed: Dec. 23, 1991

Related U.S. Application Data

[62] Division of application No. 07/588,437, Sep. 25, 1990, abandoned.

[51] Int. Cl.[6] .................................................. C07K 14/46
[52] U.S. Cl. ......................... 530/350; 530/300; 530/387; 435/69.1; 435/252.33
[58] Field of Search .................................... 530/300, 350, 530/857, 23.1, 2; 435/69.1, 69.7, 440, 320.1

[56] References Cited

U.S. PATENT DOCUMENTS

| | | | |
|---|---|---|---|
| 4,045,910 | 9/1977 | Arny et al. | 47/2 |
| 4,161,084 | 7/1979 | Arny et al. | 47/2 |
| 4,484,409 | 11/1984 | Caple et al. | 47/2 |
| 4,601,842 | 7/1986 | Caple et al. | 252/70 |
| 4,834,899 | 5/1989 | Klenecz | 252/70 |
| 4,886,663 | 12/1989 | Houghten | 424/88 |

FOREIGN PATENT DOCUMENTS

| | | |
|---|---|---|
| 8803533 | 5/1988 | WIPO . |
| 8805082 | 7/1988 | WIPO . |

OTHER PUBLICATIONS

Duman, J.G. and A. L. DeVries. 1974. Freezing resistance in winter flounder *Pseudopleronectes americanus* Nature 247:237–238.

DeVries, A.L., and Y. Lin. 1977. Biochimica et Biophysica Acta 495:388–392. Structure of a Peptide Antifreeze and Mechanism of Adsorption to Ice.

Raymond, J. A., W. Radding, and A. L. DeVries. 1977. Biopolymers 16:2575–2578. Circular Dichroism of Protein and Glycoprotein Fish Antifreezes.

Raymond, J.A., and A.L. DrVries. 1977. Proceedings of the National Academy of Sciences of the USA 74:2589–2593. Adsorption inhibition as a mechanism of freezing resistance in polar fishes.

Lin, Y. and J.K. Gross. 1981. Proceedings of the National Academy of Sciences of the USA 78:2825–2829. Molecular cloning and characterization of winter flounder antifreeze cDNA.

Knight, C.A., A. L. DeVries, and L. K. Oolman. 1984, Nature 308:295–296. Fish antifreeze protein and the freezing and recrystallization of ice.

DeVries, A. L. 1984. Philosophical Transactions of the Royal Society of London (series B) 304:575–588. Role of glycopeptides and peptides in inhibition of crystallization of water in polar fishes.

Caple, G., W.L. Kerr, T.S. Burcham, D.T. Osuga, Y. Yeh, and R.E. Feeney. 1985. Journal of Colloid and Interface Science 111:299–304. Superadditive Effects in Mixtures of Fish Antifreeze Glycoptroteines and Polyalcohols or Surfactants[1,2].

(List continued on next page.)

*Primary Examiner*—John L. LeGuyader
*Attorney, Agent, or Firm*—Whitham, Curtis & Whitham

[57] ABSTRACT

A synthetic antifreeze peptide and a synthetic gene coding for the antifreeze peptide have been produced. The antifreeze peptide has a greater number of repeating amino acid sequences than is present in the native antifreeze peptides from winter flounder upon which the synthetic antifreeze peptide was modeled. Each repeating amino acid sequence has two polar amino acid residues which are spaced a controlled distance apart so that the antifreeze peptide may inhibit ice formation. The synthetic gene has been expressed in *E. coli*. A synthetic insert fragment has been prepared which can be readily inserted into the synthetic gene to alter the number of repeating units and/or amino acid composition in the antifreeze peptide produced.

6 Claims, 10 Drawing Sheets

OTHER PUBLICATIONS

Hew, C.L., N.C. Wang, S.Yan, H.Cai, A.Sclater, and G.L. Fletcher. 1986. European Journal of Biochemistry 160:267–272. Biosysthesis of antifreeze polypeptides in the winter flounder.

Yang, D.S.C., Y.J. Chung, P. Chen, J.P. Rose, and D.L. Hew. 1986. Journal of Molecular Biology 189:725. Single Crystals of a Winter Flounder Antifreeze Polypeptide.

Bush, C.A. and R.E. Feeney, 1986. International Journal of Protein Research 28:386–397. Conformation of the glycoytripetide repeating unit of antifreeze glycoprotein of polar fish as determined from the fully assigned proton n.m.r. spectrum.

Scott, G.K., P.L. Davies, M.A. Shears, and G. L. Fletcher. 1987. European Journal of Biochemistry 168:629–633. Structural variations in the alanine–rich antifreeze proteins of the pleuronectinae.

Kao, M.H., G.L. Fletcher, N.C. Wang, and C.L.Hew 1986. Canadian Journal of Zoology 64:578–582. The relationship between molecular weight and antifreeze polypeptide activity in marine fish[1].

Yang, D.S.C., M. Sax, A. Chakrabartty, and C.L. Hew. 1988. Nature 333:232 237 Crystal structure of an antifreeze polypeptide and its mechanistic implications.

Davies, P.L. C.L. Hew, and G.L. Fletcher, 1988, Canadian Journal of Zoology 66:2617–2622. Fish antifreeze proteins: physiology and evolutionary biology.

Parody–Morreale, A., K.P. Murphy, E.Di Cera, R. Fall, A.L. Devries, and S.J. Gill. 1989. Nature 333:782–783. Inhibition of bacterial ice nucleato by fish antifreeze glycoproteins.

Cutler, A.J., M. Saleem, E. Kendall, L.V. Gusta, F. Georges, and G.L. Fletcher. 1989. Journal of Plant Physiology 135:351–354. Winter Flounder Antifreeze Protein Improves the Cold Hardiness of Plant Tissues.

Chakrabartty, A., V.S. Ananthanarayanan, and C.L. Hew. 1989. Journal of Biological Chemistry 264:11307–11312. Structure–Function Relationship in a Winter Flounder Antifreeze Polypeptide Chakrabartty, A., D.S.C. Yang, and C.L. Hew, 1989. Journal of Biological Chemistry 264:11313–11316. Structural Function Relationship in a Winter Flounder Antifreeze Polypeptide.

Knight, C.A. and A.L. DeVries. 1989. Science 245:505–507. Melting Inhibition and Superheating of Ice by Antifreeze Glycopeptide.

Raymond, J.A., P. Wilson, and A.L, Devries. 1989. Proceedings of the National Academy of Sciences of the USA 86:881–885. Inhibition of growth on nonbasal planes in ice by fish antifreezes.

Peters, I. D., C.L. Hew, and P.L. Davies, 1989. Protein Engineering 3:145–151. Biosysthesis of winter flounder antifreeze proprotein in *E.coli*.

Malcolm J. Casadaban, Joany Chou, and Stanley N. Cohen, 1980, In Vitro Gene Fusions That Join An Enzymatically Active B–Galactosidae Segment to Amino–Terminal Fragments of Exogenous Proteins: *Escherichia coli* Plasmid Vectors for the Detection and Cloning of Translational Initiation Signals; Journal of Bacteriology, p. 971, Stanford Univ. vol. 143, No. 2.

Joseph D. Schrag, Scott M. O'Grady and Arthur L. DeVries; Relationship of Amino Acid Composition and Molecular Weight of Antifreeze Glycopeptides to Non–Colligative Freezing Point Depression; 1982, Elsevier Biomedical Press, p. 322; Univ. of Illinois (No. 717).

F. William Studier & Barbara A. Moffatt: Use of Bacteriophage T7 RNA Polymerase to Direct Selective High–Level Expression of Cloned Genes; 1986; J. Mol. Biol. p. 113–130; Brookhaven National Laboratory (No. 189).

Peter O. Olins, Catherine S. Devine, Shaukat H. Rangwala & Kamilla S. Kayka; The T7 phage gene 10 leader RNA, a ribosome–binding site that dramatically enhances the expression of foreign genes in *Escherichia coli*; 1988; Elsevier Science Publishers, pp. 227–235; Monsanto Company (No. 73).

Mark Pickett, Gary Scott, Peter Davies, Nam Wang, Shashikant Joshi and Choy Hew; 1984; Sequence of an antifreeze protein precursor; Eur. J. Biochem; pp. 35–38 (No. 143).

Gourlie et al, "Winter Flounder Antifreeze Proteins: A Multigene Family," The Journal of Biological Chemistry, vol. 259, No. 23, Dec. 10, 1984, pp. 14960–14965.

Burcham et al., "Antifreeze Glycoproteins: Influence of Polymer Length and Ice Crystal Habit on Activity," Biopolymers, vol. 23, 1379–1395 (1984).

Gourlic et al. J. Biol. Chem 259:14960 (1984).

Maniatis et al. Cloning Manual, CSH (1982).

Shen et al. PNAS (1984) 81:4627–4631.

Willson et al. Gene Anal. Tech. (1985) 2:7782.

Doel et al. NAR (1980) 8:4575–4592.

Kempe et al. Gene (1985) 39:239–245.

```
        E                  B                              C                                              S
        C                  G                              L                                              S
        O                  L                              A                                              T
        R                  2                              1                                              2
        1
    ┌─GAATTCGTAGATCTGTAAGCAGGTTTATCGATGTCCACCGCTTCCGACGCCGCGGCAGCAGCAGCTGCT
  1 │                                                                                                    69
    └─CTTAAGCATCTAGACATTCGTCCAAATAGCTACAGGTGGCGAAGGCTGCGGCGCCGTCGTCGTCGACGA
   (SEQ ID No:3)   (SEQ ID No:2) MetSerThrAlaSerAspAlaAlaAlaAlaAlaAlaAla
                                                              ├──────1──────┤
```

```
      ACTGCGGCGACCGCAGCAGCGGCTGCGGCAGCTACTGCGGCGACCGCAGCAGCGGCTGCGGCAGCTACT
 70 ──────────────────────────────────────────────────────────────────────── 138
      TGACGCCGCTGGCGTCGTCGCCGACGCCGACGATGACGCCGCTGGCGTCGTCGCCGACGCCGTCGATGA
      ThrAlaAlaThrAlaAlaAlaAlaAlaAlaAlqThrAlaAlaThrAlaAlaAlaAlaAlaAlaThr
      ├───────2────────┤├────────3────────┤├────4────┤
```

```
      GCGGCGACCGCAGCAGCGGCTGCGGCAGCTACCGCTGCTACCGCAGCAGCTGCTGCGGCAGCAACTGCGGCG
139 ──────────────────────────────────────────────────────────────────────────── 210
      CGCCGCTGGCGTCGTCGCCGACGCCGTCGATGGCGACGATGGCGTCGTCGACGACGCCGTCGTTGACGCCGC
      AlaAlaThrAlaAlaAlaAlaAlaAlaAlqThrAlaAlaThrAlaAlaAlaAlaAlaAlqThrAlaAla
                        ├────4────┤├─────5─────┤├────6────┤
                                        P
                                        S
                                        T
                                        1
```

```
      ACCGCAGCAGCGGCTGCGGCAGCTACCGCAGCTACTGCAGCTAAAGCTGCGGCTCTGACTGCTGCAAAC
211 ─────────────────────────────────────────────────────────────────────── 279
      TGGCGTCGTCGCCGACGCCGTCGATGGCGTCGATGACGTCGATTTCGACGCCGAGACTGACGACGTTTG
      ThrAlaAlaAlaAlaAlaAlaAlaThrAlaAlaThrAlaAlaLysAlaAlaAlaLeuThrAlaAlaAsn
      ├──────6──────┤├──────7──────┤├────8────┤
                                              B
                                              A
                                              M
                                              H
                                              1
```

```
      GCAGCGGCTGCTGCGGCGGCGACTGCTGCGGCAGCGGCTCGTGGTTGATAAGGATCC
280 ────────────────────────────────────────────────────────── 336
      CGTCGCCGACGACGCCGCCGCGTGACGACGCCGTCGCCGAGCACCAACTATTCCTAGG (SEQ ID No:4)
      AlaAlaAlaAlaAlaAlaAlaThrAlaAlaAlaAlaAlaArgGly * *
      ├──────8──────┤
```

(SEQ ID No:9)
5' - GCT GCG GCC GCG GCA GCC ACC GCA GCA ACT GCA - 3'
3' - A CGT CGA CGC CGG CGC CGT CGG TGG CGT CGA TG - 5'
(SEQ ID No:11) — rAlaAlaAlaAlaAlaAlaAlaThrAlaAlaTh
(SEQ ID No:10)

FIG.6

(SEQ ID No:12)
5' - GCT GCG GCC GCG GCA GCC ACC GCA GCA ACT GCA GCT GCG GCC GCG GCA GCC ACC GCA GCA ACT GCA - 3'
3' - A CGT CGA CGC CGG CGC CGT CGG TGG CGT CGG CGT CGA TGA CGT CGA CGC CGG CGC CGT CGG TGG CGT CGT TG - 5'
(SEQ ID No:12)

FIG.7

(SEQ ID No:14)
5' - GCT GCG GCC GCG GCA GCC TGC GCA GCA  ACT GCA - 3'
3' - A CGT CGA CGC CGG CGC CGT CGG ACG CGT CGA TG - 5'
(SEQ ID No:15)

A.
(SEQ ID No:16)
                 EcoRI              CIaI                 SstII
5' - GTGTGAATTCGTAGATCTGTAAGGAGGTTTATCGATGTCCACCGCTTCCGACGCCGCGGTACCGAGG-3'
(SEQ ID No:18) ***AlaGlyLeuSerMetSerThrAlaSerAspAlaAlaAlaAlaAla

3' - CACACTTAAGCATCTAGACATTCCTCCAAATAGCTACAGGTGGCGAAGGCTGCGGCGCCATGGCTCC -5'
                                         FIG.8A            KpnI
                                                                 (SEQ ID No:17)

B1.
                              PvuII
(SEQ ID No:19) — 5' - GGCAGCAGCAGCTGCTACTGCTGCCACCG -3'
(SEQ ID No:21) — aAlaAlaAlaAlaAlaThrAlaAlaThrA
              3' - CGCCGTCGTCGTCGACGATGACGACGGT — (SEQ ID No:20)
                 SstII
                                FIG.8B

B2. (SEQ ID No:22)                                                  XmaIII
5'- CAGCGGCGGCTGCGGCAGCTACTGCGGCGACCGCAGCAGCGGCTGCGGCAGCTACTGCGGCGAC-3'
(SEQ ID No:24) —laAlaAlaAlaAlaAlaAlaThrAlaAlaThrAlaAlaAlaAlaAlaAlaAlaThrAlaAlaTh
3' - GGCGTCGCCGCCGACGCCGTCGATGACGCCGCTGGCGTCGTCGCCGACGCCGTCGATGACGCCGCTGCCGGC-5'
                                FIG.8C                    (SEQ ID No:23)

B3.
(SEQ ID:No:25) BalI                 PvuII               HaeIII
5'-GGCCGCAGCGGCTGCGGCAGCTACCGCTGCTACCGCAGCAGCTGCTGCGGCAGCAACTGCGG-3'
(SEQ ID No:27) — rAlaAlaAlaAlaAlaAlaAlaThrAlaAlaThrAlaAlaAlaAlaAlaAlaAlaThrAlaA
        3'-GTCGCCGACGCCGTCGATGGCGACGATGGCGTCGTCGACGACGCCGTCGTTGAGGCC-5'
     XmaIII
   HaeIII                         FIG.8D               (SEQ ID No:26)

B4.                                                       PstI
(SEQ ID No:28) — 5'-CCACCGCAGCAGCGGCTGCGGCAGCTACCGCAGCTACTGCA-3'
(SEQ ID No:30) — laThrAlaAlaAlaAlaAlaAlaAlaThrAlaAlaThrAla
        3'-GGTGGCGTCGTCGCCGACGCCGTCGATGGCGTCGATG-5' (SEQ ID No:29)
    HaeIII
                                FIG.8E

C.

(SEQ ID No:31)
5'-GCTAAAGCTGCGGCTCTGACTGCTGCAAACGCAGCGGCTGCTGCGGCGGCGACTGCTGCGGCAGCGGCTCGT-
-AlaLysAlaAlaAlaLeuThrAlaAlaAsnAlaAlaAlaAlaAlaAlaThrAlaAlaAlaAlaArg-
3'-ACGTCGATTTCGACGCCGAGACTGACGACGTTTGCGTCGCCGACGACGCCGCCGCTGACGACGCCGTCGCCGAGCA-
PstI
(SEQ ID No:33)

BamHI
-GGTTGATAAG-3'
-Gly******
-CCAACTATTCCTAG-5'  (SEQ ID No:32)

FIG.8F

CΔl
(SEQ ID No:34)
5'-GCTAAAGCTGCGGCTCTGACTGCTGCAAACGCAGCGGCTGCTGCGGCGGCGACTGCTGCGGCAGCGGCTCGT- (SEQ ID No:36) -AlaLysAlaAlaAlaLeyThrAlaAlaAsnAlaAlaAlaAlaAlaAlaThrAlaAlaAlaAlaArg-
3'-ACGTCGATTTCGACGCCGAGACTGACGACGTTTGCGTCGCCGACGACGCCGCCGCTGACGACGCCGTCGCCGAGCA-
PstI

-GGTTGTAAG-3'
-GlyCysLysAspP
-CCAACATTCCTAG-5'  (SEQ ID No:35)
BamHI

FIG.8G

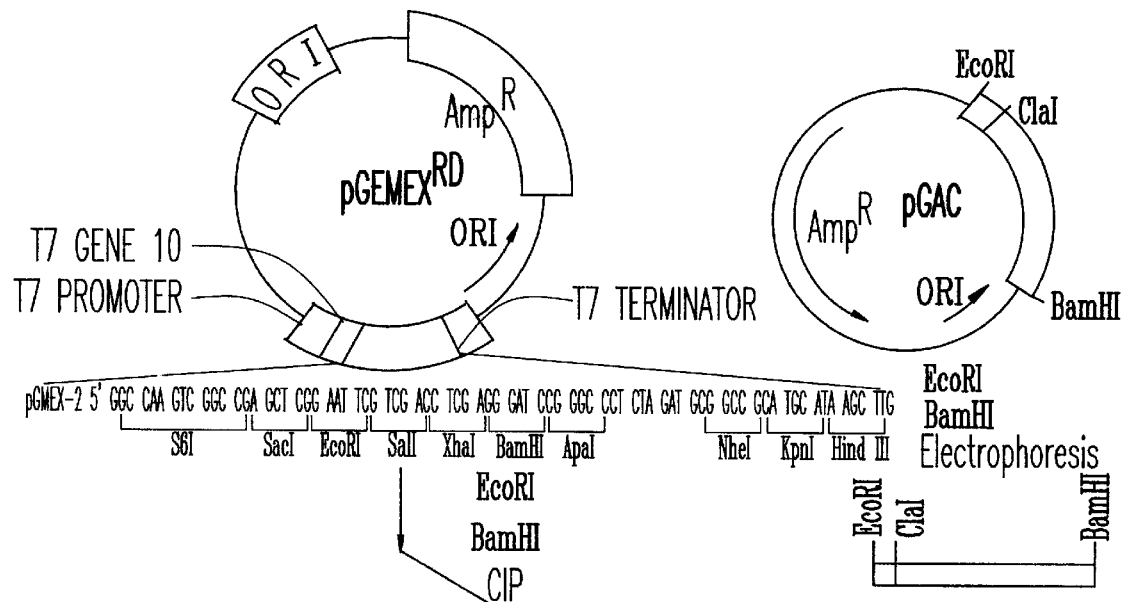
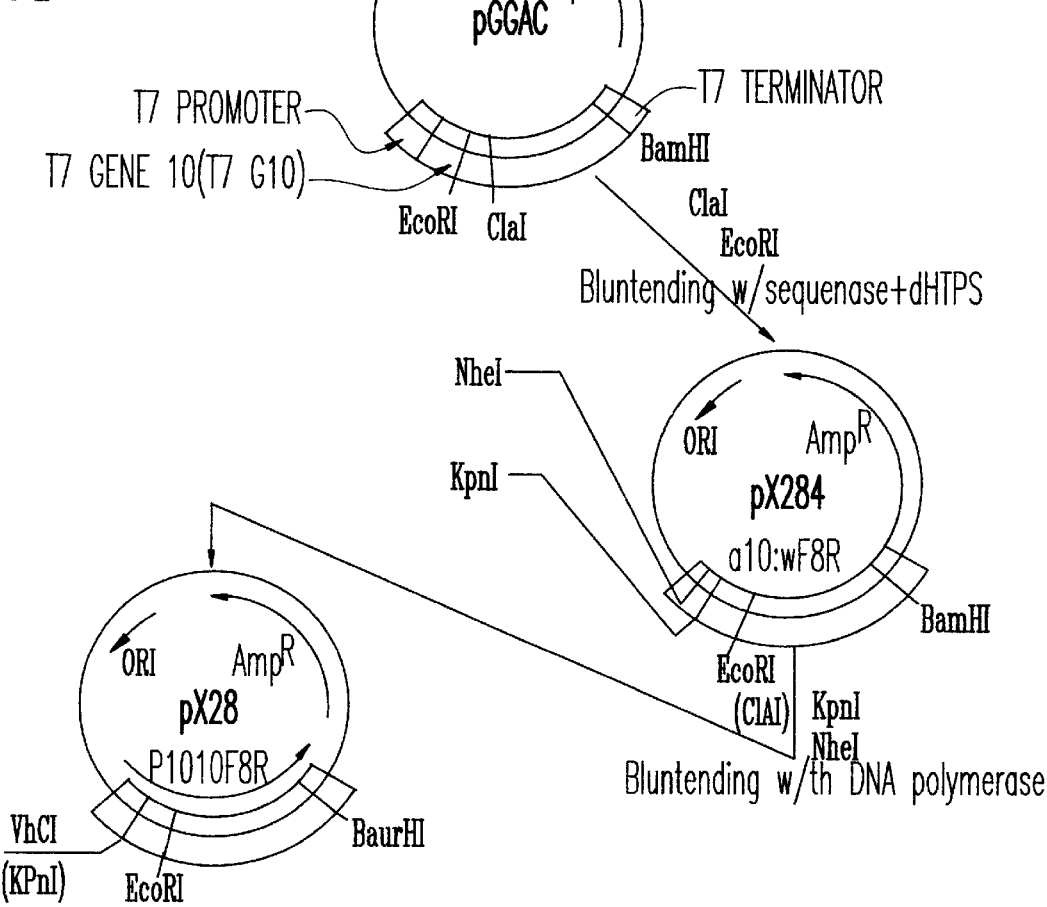
FIG. 9B (SEQ ID NO:37) EcoRI SstII
5'-AATTCAGATCTGCGAGATACCGCTTCCGACGCCGC-3'
(SEQ ID NO:39)———AsnSerAspLeuArgAspThrAlaSerAspAlaAl
3'-GTCTAGACGCTCTATGGCGAAGGCTGCGG-5'—(SEQ ID NO:38)

FIG.10

SYNTHETIC ANTIFREEZE PEPTIDE

This patent application is a divisional of the U.S. patent application filed Sep. 25, 1990, having Ser. No. 07/588,437, now abandoned, and is related to the co-pending file wrapper continuation application of of Ser. No. 07/588,437 which has Ser. No. 07/814,220 and was filed on even date herewith, and both of those patent applications are herein incorporated by reference.

BACKGROUND OF THE INVENTION

1. Field of the Invention

The present invention generally relates to compositions used to prevent ice formation and, more particularly, to a synthetic polypeptide which lowers the freezing point of water and a synthetic gene for producing the polypeptide in bacteria.

2. Description of the Prior Art

Ice formation is an ever present problem in today's world. Ice on roadways and bridges is believed to be the cause of numerous automobile accidents. Ice on aircraft wings is known to decrease lift and increase the weight of the aircraft and is believed to be responsible for causing at least one jumbo jet to crash land. Ice continually forms on the decks of boats which sail in arctic and antarctic waters, thereby making operations aboard the boats extremely hazardous. Ice caused during severe weather can also result in millions of dollars worth of damage to crops such as grapefruits and oranges.

Ice prevention in the roadway, bridge, and boat environments typically involves applying large amounts of toxic chemicals such as glycols and salts to ice formed on the surfaces of the roadway, bridge or boat. Application of glycols and salts is reactive in nature since the conditions for ice formation must all ready be present when the glycols and salts are applied. The chemicals used for ice prevention can be harmful to the environment and tend to cause rust formation on automobiles which travel over the salt covered roadways. Ice prevention in aircraft usually involves onboard inflatable members and heating elements which break and melt the ice after it forms. Such ice protection schemes require energy and are only suitable for specific applications. Presently, there is no generally accepted ice prevention scheme used in agriculture.

Efforts have been made to find less toxic alternatives for ice prevention which are suitable for ice prevention/suppression in a wide variety of applications. U.S. Pat. Nos. 4,045,910 and 4,161,084 to Arny et al. disclose protecting plants from frost damage by applying non-ice nucleating bacteria to the plants before the onset of freezing cold. The non-ice nucleating bacteria are supposed to compete with native ice nucleating bacteria and prevent ice formation by reducing the number of potential "triggers" to crystallization. One drawback of the Arny et al. ice prevention method is that it involves the release of genetically modified bacteria into the environment. U.S. Pat. No. 4,484,409 to Caple et al. discloses chemically synthesizing polymeric ice nucleation inhibitors via free radical polymerization. The polymers produced in Caple et al. have a tightly controlled spacing of about 15 Angstroms (Å) between the hydrophobic and hydrophilic groups. The polymers are sprayed on the plants and are designed to inhibit ice formation. U.S. Pat. No. 4,834,899 to Klevecz discloses applying a bactericide to plants to prevent frost damage by killing the ice nucleating bacteria. U.S. Pat. No. 4,601,842 to Caple et al. discloses applying a proteinaceous material obtained from cold weather plants to growing crops for protection from frost damage.

Recently, naturally produced antifreeze materials that are present in cold water fish have been investigated for their utility as ice supressors (see, for example, Pickett et al., *Eur. J. Biochem.* 143:35–38 (1984)). These materials are either peptides or glycopeptides and have been designated as AFPs for "antifreeze peptides" and AFGPs for "antifreeze glycopeptides", respectively. The AFPs and AFGPs are produced by the fish to prevent the formation of ice in their body fluids so that they may survive in water temperatures below freezing. There are several subclassifications of AFPs and AFGPs, with the simplest being the alanine rich peptides found in several species of flounder.

FIG. 1 shows the primary amino acid sequence of a native AFP isolated from the winter flounder Pseudopleuronectes americanus (see, DeVries, *Phil. Trans. of the Roy. Soc. of London* (*series B*) 304:575–588 (1984)). This is a class 1 or alanine rich AFP. There are 38 amino acids (SEQ ID NO:1) in the AFP with the last 33 amino acids comprising essentially 3 repeats of 11 amino acids (i.e., there are slight differences in the repeating groups where, for example, leucine (leu) is substituted for alanine (ala) and another polar amino acid (xaa) can be substituted for aspartic acid (asp)). The non-polar amino acids, i.e., ala and leu, are used primarily as "spacers" which position the polar amino acids, i.e., thr and asp, approximately 4.5 angstroms (Å) apart. The AFP of SEQ ID NO:1 is but one example of a wide variety of AFPs. Most naturally occurring class 1 AFPs are approximately 70% ala and include three to five repeats of a sequence which includes two amino acids capable of hydrogen binding, i.e., thr and asp, spaced approximately 4.5 Å apart. Chakrabartty et al., in *Journal of Biological Chemistry* 264:11307–11312 (1989) and 264:11313–11316 (1989), disclosed the direct chemical synthesis of AFPS. It was determined in Chakrabartty et al. that the minimum size for activity of an AFP is 3 repeats of the sequence. There are no known naturally produced AFPs that include greater than 5 repeats of the sequence.

FIG. 2, which is taken from the above cited DeVries article, shows an AFP interacting with an ice crystal during ice formation. As shown in FIG. 2, the secondary structure of a class 1 AFP is an alpha helix and the tertiary structure is a straight rod. The polar amino acids, thr and asp, are positioned on one side of the rod and form hydrogen bonds with the water molecules along the α-axis of the ice crystal. The 4.5 Å spacing of the polar amino acids in the AFP is precisely the spacing of water molecules in a forming ice crystal.

FIGS. 3a and 3b, which are also taken from the above-cited DeVries article, shows that ice crystals form in two directions. The crystals grow outward along the α-axis and at right angles to this plane along the c-axis. By binding to the forming prism faces in the α-axis, the AFPs disrupt the formation of the step, thereby preventing smooth formation of the face, and resulting in curved fronts. Site 10 shows an area where two AFP molecules have bound closely together which has resulted in an even more effective blockage of ice crystal growth. The same extra blockage effect would occur with a longer molecule that can block more of the step.

The mechanism of ice crystal growth suppression by AFPs illustrated in FIGS. 2 and 3b falls under the "adsorption inhibition hypothesis" proposed by DeVries. As illustrated, the ice crystal can only grow in unblocked regions because the presence of the AFP ties up the potential insertion sites for new water to come into the lattice. In theory, since all water adds to the lattice by hydrogen bonding too, if all possible active sites are bound up, the AFPs must by moved out of the way before new water can be added. Attachment of the AFP to the ice crystal increases the ratio of molecular volume to surface area, and in order for freezing to occur, more energy must be removed from the system than would be required in the absence of the AFPS. Hence, the freezing point of water is lowered by the binding action of AFPs. The mechanism of action of AFPs is somewhat analogous to "poisoning" the growth of a crystal by the presence of an impurity where the AFP acts as the impurity. Melting point, however, is not lowered, and this phenomenon, which has been known for many years, is referred to as "thermal hysteresis". Freezing point depression is not a colligative reaction, i.e., very low concentrations of AFP in pure solutions are known to have approximately five hundred times greater depression than colligative processes would predict.

Ideally, AFPs could be used to suppress ice formation in a wide variety of environments. AFPs have the advantage that they can be applied to a road surface or to an agricultural plant ahead of time so that they would interact with ice during formation and, further, they can be applied after the onset of ice formation and serve to prevent continued ice crystal formation. In addition, since AFPs are simply polypeptide chains, they pose no hazard to the environment. In winter flounder, the concentration of AFPs range from 1.0% to 3.0% depending on the species and the season; hence, AFPs are not produced in large enough quantities in fish for the fish to be harvested as a source for an ice preventing agent. Moreover, AFPs and AFGPs are typically only produced in the fish during the winter months. As noted above, Chakrabartty et al. have shown it is possible to synthesize AFP using direct chemical processes; however, these processes can be expensive and time consuming. Peters et al., in *Protein Engineering* 3:145–151 (1989), disclosed producing a semisynthetic winter flounder AFP in Escherichia coli (*E. coli*). In Peters et al, a gene constructed of a fused synthetic deoxyribonucleic acid (DNA) fragment and a DNA fragment derived from a full length winter flounder clone was inserted into a plasmid and the plasmid was placed in the *E. coli* for production of a fusion protein. The biosynthetic fusion protein produced contained part of a pro-AFP and part of a β-galactosidase peptide and had limited antifreeze activity after cleavage from β-galactosidase. What is needed is a synthetic polypeptide which has greater freezing point depression capability than those AFPs which occur in nature and which can be economically produced by biosynthetic processes.

SUMMARY OF THE INVENTION

It is therefore an object of the present invention to provide a new AFP modeled after the native AFP found in the winter flounder, Pseudopleuronectes americanus, but which is longer than the native AFP and should have greater ability to suppress ice formation than that which can be achieved by solutions of the native AFP.

It is another object of this invention to provide a gene coding for the new AFP which can be expressed in a bacterial host.

It is yet another object of this invention to provide a deoxyribonucleic acid (DNA) insert sequence which can be easily placed in the gene coding for the new AFP which ultimately will extend the length of new AFP produced by the bacterial host and may provide for the crosslinking of separate polypeptide chains.

According to the invention, an artificial peptide with a specific sequence of amino acids modeled after an AFP found in the winter flounder, Pseudopleuronectes americanus, has been designed. The gene necessary to produce the artificial AFP has been synthesized and inserted into *E. coli*, and the gene has been expressed in the *E. coli*. In addition, a DNA insert sequence has been synthesized which can be readily inserted into the gene for producing the artificial AFP and serves the function of extending the length of the AFP ultimately produced by the bacterial host and may provide for the crosslinking of separate polypeptide chains.

BRIEF DESCRIPTION OF THE DRAWINGS

The foregoing and other objects, aspects and advantages will be better understood from the following detailed description of a preferred embodiment of the invention with reference to the drawings, in which:

FIG. 4 is a base pair sequence of a synthesized gene wf8r and a synthesized amino acid sequence for an AFP polypeptide WF8R wherein the gene wf8r codes for the AFP WF8R;

FIG. 5 is a 33 base pair sequence of a DNA insert fragment which can be inserted in the wf8r gene of FIG. 4 at the PST1 restriction site which extends the length of WF8R AFP by one repeating unit to produce WF9R;

FIG. 6 is a 66 base pair sequence of a dimer of the DNA insert fragment shown in FIG. 5;

FIG. 7 is a 33 base pair sequence of a DNA insert fragment similar to that shown in FIG. 5, but in which a threonine codon has been replaced with a cysteine codon to enable cross-linking of two AFP chains through disulfide bridges;

FIGS. 8a–8g are seven synthetic restriction fragments which were used in the process of producing the gene shown in FIG. 4;

FIGS. 9a–9c are flow diagrams for constructing the gene shown in FIG. 4 from the six synthetic restriction fragments shown in FIGS. 8a–8f; and FIG. 10 is a synthetic restriction fragment which will be used to modify the gene shown in FIG. 4 to make the N-terminal amino acids of the WF8R protein after digestion with Clostripain identical to the N-terminal amino acids of the native flounder AFP.

DETAILED DESCRIPTION OF A PREFERRED EMBODIMENT OF THE INVENTION

Figure 1:
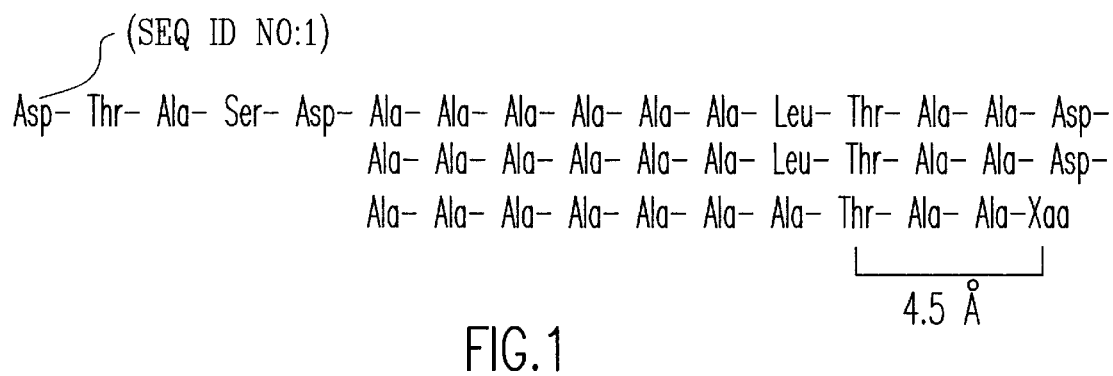
FIG. 1 is the primary amino acid sequence of an AFP found in the winter flounder Pseudopleuronectes americanus.
Figure 2:
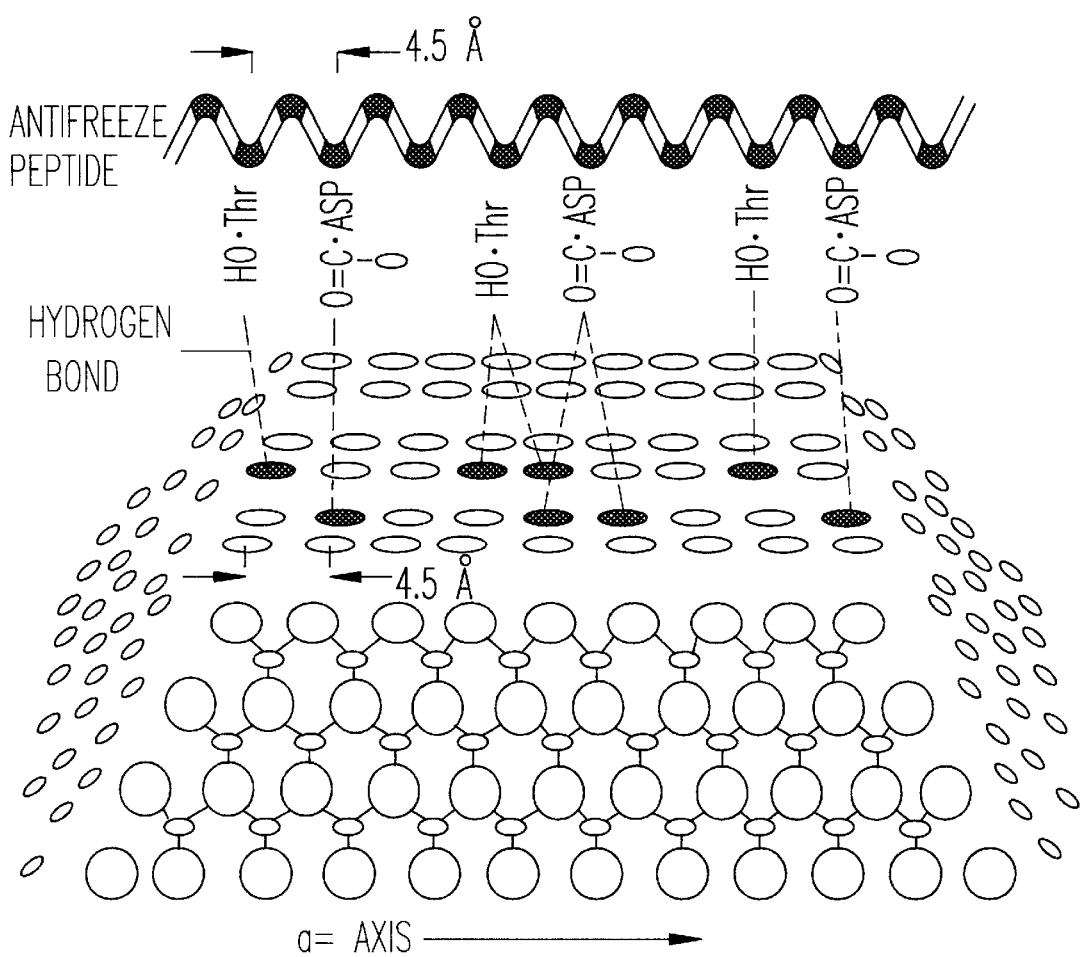
FIG. 2 is a representational drawing of a forming ice crystal and an antifreeze peptide showing how the spacing allows hydrogen bonding to the face of the forming ice crystal.
Figure 3A:
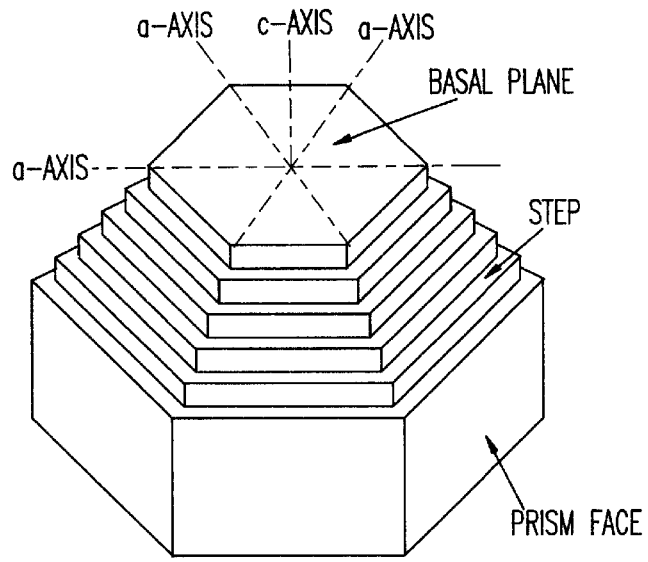
FIGS. 3a and 3b are isometric views of a forming ice crystal and ice crystal with AFPs bound to steps thereon, respectively, which together show how AFPs interact with the forming ice crystal step according to the adsorption inhibition hypothesis.
Figure 3B:
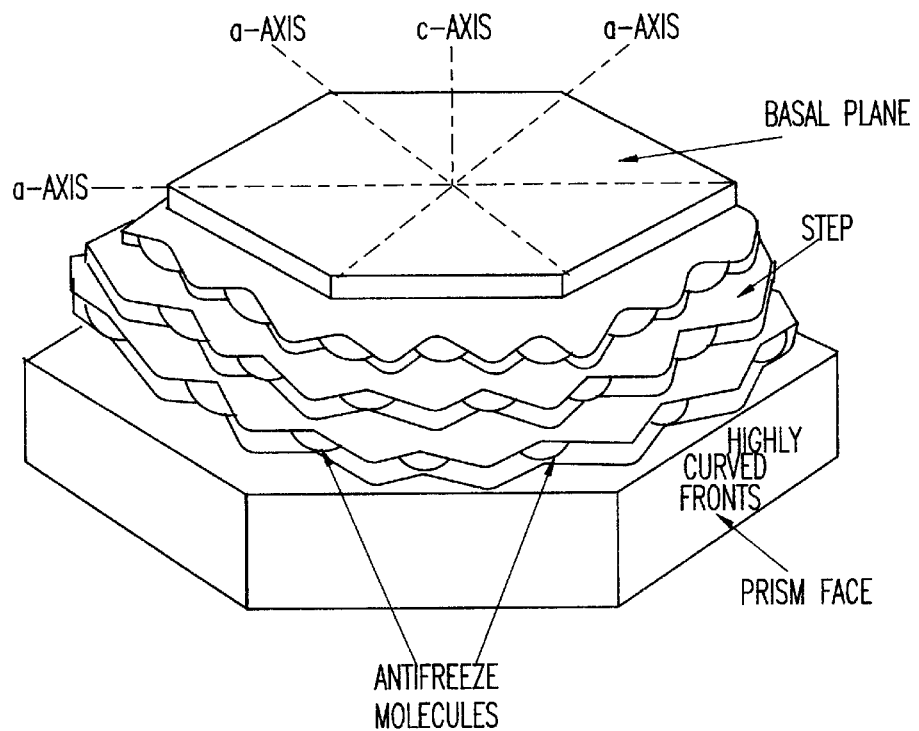

Referring now to the drawings, and more particularly to FIG. 4, there is shown a synthetic AFP peptide (SEQ ID NO:2) and a synthetic gene (comprised of DNA SEQ ID NO:3 and DNA SEQ ID NO:4) coding for the AFP peptide having SEQ ID NO:2. The inventors have successfully synthesized the gene (SEQ ID NO:3 and 4) having 336 nucleotides and expressed the gene in *E.coli* and have produced the AFP peptide (SEQ ID NO:2) having 98 amino acids according to the methods discussed below in the experimental section. The synthetic gene was too large to be produced as a single piece and was constructed from several subfragments; therefore, the restriction endonuclease sites (i.e., ECORI, BGL2, CLA1, SST2, PST1, and BAMH1) where the subfragments were ligated together to form the synthetic gene are indicated above SEQ ID NO:3. Stars denote termination codons in the synthetic gene.

The AFP peptide in FIG. 4 includes five repeats of the following eleven amino acid sequence: thr-ala-ala-thr-ala-ala-ala-ala-ala-ala-ala-(SEQ ID NO:5). The repeating SEQ ID NO:5 amino acid sequences are indicated by numbered blocked regions 2–6. In addition, the AFP peptide includes the following three amino acid sequences: -thr-ala-ser-asp-ala-ala-ala-ala-ala-ala-ala (SEQ ID NO:6) indicated as blocked region 1, -thr-ala-ala-thr-ala-ala-lys-ala-ala-ala-leu- (SEQ ID NO:7) indicated as blocked region 7, and -thr-ala-ala-asn-ala-ala-ala-ala-ala-ala-ala-(SEQ ID NO:8) indicated as blocked region 8.

A key feature of the synthetic and the native AFP is that there are several repeating eleven amino acid sequences, each of which typically includes two polar amino acids spaced apart by two nonpolar amino acids. The applicants are herein defining polar amino acids as those with side chains are capable of forming hydrogen bonds and nonpolar amino acids as those with side chains not capable of forming hydrogen bonds. In the synthetic and the native AFPs, the nonpolar amino acids are usually alanine (ala) molecules; however, other nonpolar amino acids such as valine (val), isoleucine (ile), leucine (leu), glycine (gly), etc., could easily be substituted for the ala molecules in the amino acid sequence. In the synthetic and the native AFPs, the polar amino acids are usually threonine (thr) or aspartic acid (asp); however, other polar amino acids such as asparagine (asn), glutamine (gln), glutamic acid (glu), serine (ser), etc., could easily be substituted for the thr and as molecules in the amino acid sequence. The nonpolar amino acids serve as spacers to position the polar amino acids 4.5 Å apart in free space. As discussed above, the positions of the polar amino acids allows the AFP polypeptide to form hydrogen bonds with the forming ice crystal in competition with free water molecules and, thereby, block the steps for growth of the ice crystal. This process according to the "adsorption inhibition hypothesis", in essence lowers the freezing point of water.

Seven of the eight repeating eleven amino acid sequences in FIG. 4, indicated by blocks 2–8 (SEQ ID NOs:5,7,8), fit the description of having a first polar amino acid, a second and third nonpolar amino acid, a fourth polar amino acid, and fifth through eleventh nonpolar amino acids. The eleven amino acid sequence indicated by block 1 (SEQ ID NO:6) differs from the sequences in blocks 2–8 only in that the third amino acid is a serine molecule. Serines, of course, are polar molecules which include a hydroxy group. The serine molecule in block 1 is present in the native winter flounder AFP and its function is not precisely known; however, because it is smaller than the adjacent aspartic acid molecule, it is believed that the serine acts more like a nonpolar spacer and does not affect the hydrogen bonding of the threonine and aspartic acid molecules in the block 1 eleven amino acid sequence.

Each of the repeating eleven amino acid sequences in the synthetic AFP shown in FIG. 4 is dipolar in character, i.e., one end of the eleven amino acid sequence includes seven adjacent nonpolar amino acids and the other end generally includes two polar amino acids spaced apart by two nonpolar amino acids. The native AFP includes a similar dipolar arrangement in each of its repeating eleven amino acid units. It is believed that the charge interactions of the dipolar AFP polypeptide may have some effect on the hydrogen bonding capability of the AFP and on its correct orientation relative to the face of the ice crystal prior to binding with it.

A major distinction between the synthetic AFP shown in FIG. 4 and native AFP found in winter flounder is the number of repeats of the eleven amino acid sequence containing the nine nonpolar amino acids and two polar amino acids. In the native AFP, the eleven amino acid sequence is repeated three to five times, but is not known to repeat more than five times in any known organism. In the synthetic AFP, the eleven amino acid sequence is repeated seven or eight times depending on how the function of the serine residue in the first block is understood.

As discussed above, there appears to be a relationship between AFP size and freezing point depression activity. If too small a region is blocked by an AFP on the forming ice crystal, the increase in the free energy barrier would be insignificant. In fact, in Chakrabartty et al, *J. Bio. Chem.* 264:11313–11316 (1989), it was reported that chemically synthesized AFP analogs with a minimum of three repeats of the basic sequence are required for ice suppression activity. Hence, larger molecules with a greater number of repeating sequences which can form a larger amount of hydrogen bonds should be more effective in preventing ice crystal growth. This phenomena is observed in natural systems where lower molecular weight antifreezes are less effective than high molecular weight antifreezes (see, Burcham et al., *Biopolymers* 23:1379–1395 (1984) and Schrag et al., *Biochemica et Biophysica Acta* 717: 322–326 (1982). There is also evidence that on a molar basis, larger molecules are more effective in ice suppression than smaller ones. Kao et al., in *Can. J. Zool.* 64:578–582 (1986), pointed out that when the thermal hysteresis curves for peptide antifreezes are compared on a molar basis, the activity increases with increasing molecular weight. Scott et al., in *Eur. J. Biochem.* 168:629–633 (1987), analyzed various protein antifreezes from two different flounder species and have speculated that the reduced activity from the yellowtail (Limanda ferruginea) might be attributed to its size and smaller number of active sites compared to the AFP found in P. americanus.

The applicants' synthesis of the AFP polypeptide shown in FIG. 4 in a bacterial host using the synthetic gene of FIG. 4 represents a significant advance over the previous methods of producing AFP polypeptides. Chakrabartty et al., *J. Bio. Chem.* 264:11313–11316 (1989), have only contemplated making extended chains of AFPs by direct chemical synthesis which is a more cumbersome process than biosynthetic techniques. Peters et al., in *Protein Engineering* 3:145–151 (1989), merely contemplated semisynthetic AFP where the native genes encoding for an AFP were inserted into a bacterial host for production of the AFP by biosynthetic techniques. However, the Peters et al. biosynthetic technique can only result in the bacteria producing AFPs having only 3–5 repeats of the eleven amino acid sequence responsible for blocking the steps in ice formation, since no known native system has more than 5 repeats of the sequence. It was the applicants' foresight to design a completely new AFP polypeptide with a greater number of repeating sequences than the AFPs found in nature. The larger AFP polypeptide molecule has a greater number of hydrogen bonding sites and should result in greater depression of the freezing point of water than natural AFPs can achieve. Hence, the synthetic AFP should be more suitable to use in colder environments such as boat decks, airport runways, and agriculture.

Another important feature of the applicants invention is that the DNA sequence shown in FIG. 4 can readily be altered to create synthetic AFPs of even greater lengths than the AFP shown in FIG. 4. The applicants have synthesized the double stranded DNA insert fragment shown in FIG. 5 wherein the two strands are represented by SEQ ID NO:9 and SEQ ID NO:10 and each strand has 33 nucleotides. The insert shown in FIG. 5 has sticky ends which are readily compatible with the PSTI restriction endonuclease site PST1 in the synthetic gene shown in FIG. 4. As can be seen by analyzing FIGS. 4 and 5 simultaneously, the sequence of 11 amino acids (SEQ ID NO:11 in FIG. 5), where the first and last nucleotides code for only part of the threonine amino acid, insertion of this 33 base pair fragment into the synthetic gene at the PST1 site according to well known biosynthetic techniques will regenerate a PST1 site at each end of the fragment in the newly created gene wf9r. Furthermore, insertion will add a single repeat of the eleven amino acid sequence resulting in a 9 repeat AFP "WF9R". The insert fragment of FIG. 5 has been designed such that the spacing of the threonine residues is maintained and no frame shifts occur.

An added advantage of the insert fragment shown in FIG. 5 is that it is capable of "self polymerization". That is, monomeric insert oligonucleotides like those shown in FIG. 5 can be ligated end to end to produce dimeric, trimeric and polymeric forms without losing the PST1 compatible ends present in the monomer. FIG. 6 shows an example of a dimer of the FIG. 5 sequence comprised of SEQ ID NO:12 and SEQ ID NO:13 where the ends of the dimeric form are identical to those of the monomer. Polymerized forms can easily be separated by size on gels and inserted in the PST1 site of the original WF8R sequence, creating "WF12R", "WF25R", etc., forms of the AFP.

It should not be lost on the reader that while the insert fragments shown in FIGS. 5 and 6 add additional repeats of the eleven amino acid sequence responsible for hydrogen bonding to steps on an ice crystal, the AFP produced could merely be lengthened without adding additional repeating eleven amino acid sequences simply by inserting any 33 base pair nucleotide sequence having ends compatible with the PST1 site. If this is done, the spacing of the threonine residues is maintained and no frame shifts occur. Hence, the AFP produced will have the same first six repeating eleven amino acid sequences which can hydrogen bond to an ice crystal as in the WF8R of FIG. 4, an elongated polypeptide region of any particular quality desired, and the same eighth repeating eleven amino acid sequence as in the WF8R of FIG. 4.

Further in this line of reasoning, the applicants have determined that it would be quite easy to incorporate one or more cysteine residues into the sequence of an artificial AFP. If this were done, and if each such cysteine containing chain maintained a normal (i.e., active) tertiary structure, then under appropriate conditions two such chains could cross link via disulfide bridges to create a double chained quaternary structure consisting of two otherwise independent AFP molecules. Such a molecule would carry twice as many potential sites for hydrogen bonding. Assuming each chain retained freezing point depression activity, such a molecule, when hydrogen bonded to a forming ice crystal, would cover more of a forming crystal face than a single chain would. Hence, the surface area/volume ratio should be more affected than with a single chain AFP, thus depressing the freezing point still further than with single chain molecules of equivalent length.

FIG. 7 shows a double stranded DNA insert fragment (SEQ ID NO:14 and SEQ ID NO:15) which can be used to produce multi-chain synthetic AFPs. The DNA insert fragment is very similar to the DNA insert fragment shown in FIG. 5 except that one of the threonine codons (i.e., ACC) has been replaced with a cysteine codon (i.e, TGC) in the seventh position (indicated by a star). One such cross-linkable fragment can be included placed in the gene shown in FIG. 4 at the PST1 site. If desired, the process of polymerization described in conjunction with FIG. 6 could be carried out with the fragment of FIG. 7 so that AFPs with more than one disulfide link could be created. The elongated single chain AFPs containing the cysteine residues will be expressed in bacteria, and later linked through the formation of interchain disulfide bridges after purification.

EXAMPLE

Figure 9A:
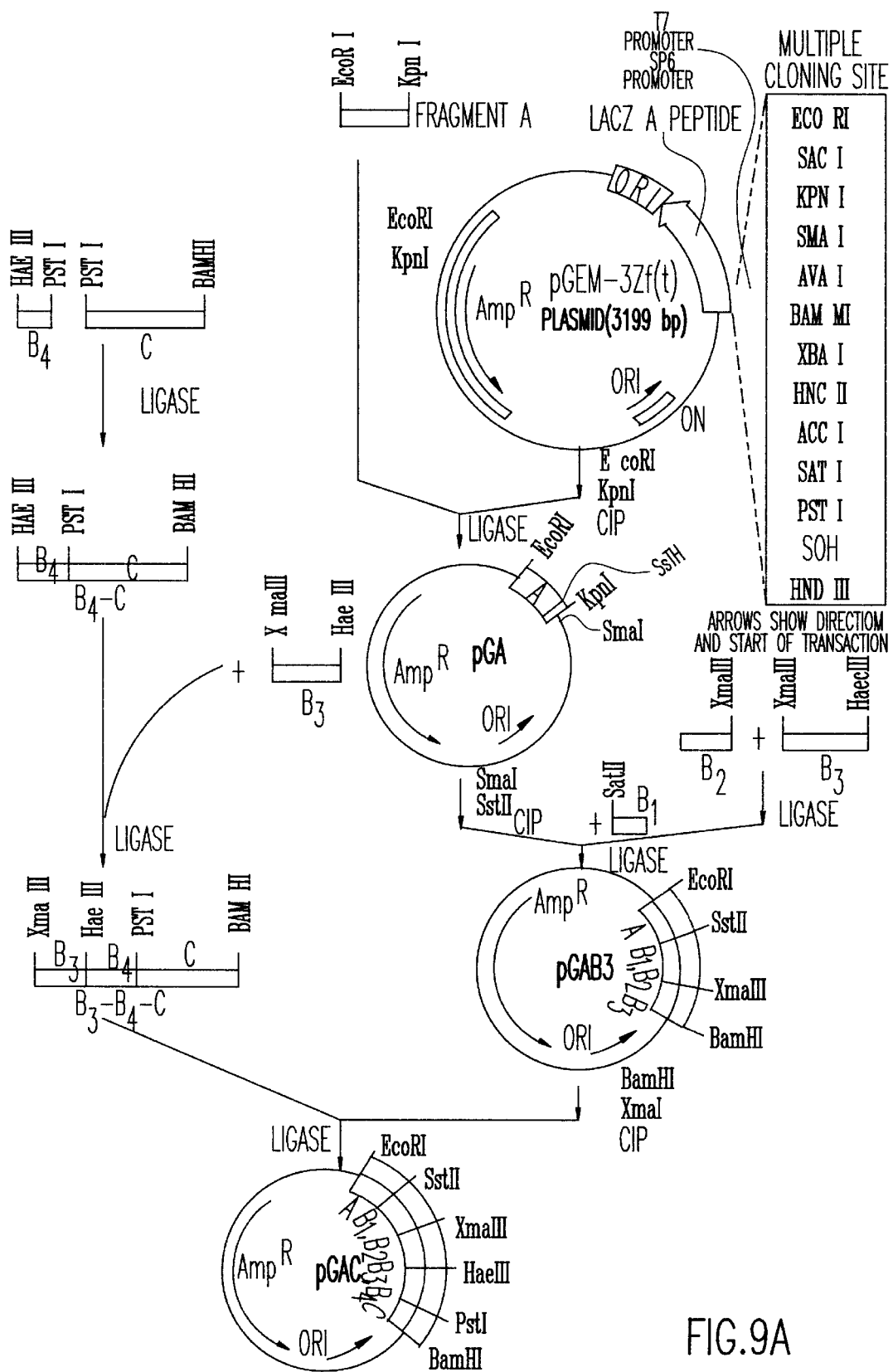
Figure 9C:
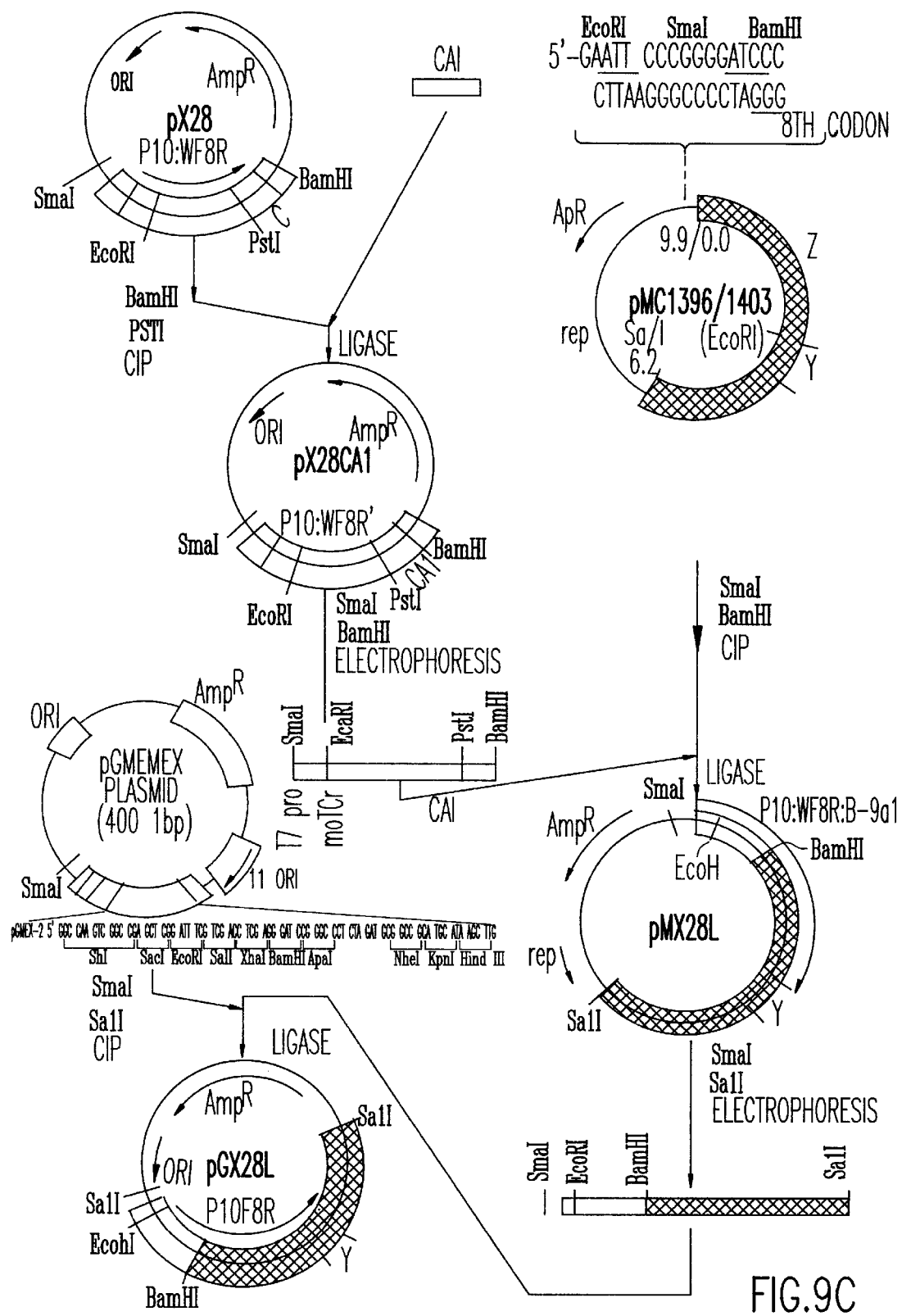

The following defines the synthesis of the wf8r gene shown in FIG. 4 and its expression in *Escherichia coli:*
Assembly of the wf8r coding sequence The structural part of the wf8r gene was assembled from six synthetic double stranded DNA restriction fragments: A, $B_1$, $B_2$, $B_3$, $B_4$, C and CΔ1 shown respectively in FIGS. 8a–8g. In each of the fragments A, $B_1$, $B_2$, $B_3$, $B_4$, C and CΔ1 the internal restriction enzyme recognition sites are indicated by lines above the sequences and the digestion pattern for each of these enzymes is indicated by small vertical arrows. Each of the fragments was commercially synthesized as two single-stranded oligonucleotides by the Promega Co. of Madison, Wis. FIG. 8a shows that fragment A is constructed from SEQ ID NO:16 and SEQ ID NO:17 and partially codes for SEQ ID NO:18. The stars denote termination codons. FIG. 8b shows that fragment $B_1$ is constructed from SEQ ID NO:19 and SEQ ID NO:20 and codes for SEQ ID NO:21. FIG. 8c shows that fragment $B_2$ is constructed from SEQ ID NO:22 and SEQ: ID NO:23 and codes for SEQ ID NO:24. FIG. 8d shows that fragment $B_3$ is constructed from SEQ ID NO:25 and SEQ ID NO:26 and codes for SEQ ID NO:27. FIG. 8e shows that fragment $B_4$ is constructed from SEQ ID NO:28 and SEQ ID NO:29 and codes for SEQ ID NO:30. FIG. 8f shows that fragment C is constructed from SEQ ID NO:31 and SEQ ID NO:32 and codes for SEQ ID NO:33. FIG. 8g shows that fragment CΔ1, which is very similar except for the ending to fragment C in FIG. 8f, is constructed from SEQ ID NO:34 and SEQ ID NO:35 and codes for SEQ ID NO:36. The complimentary oligonucleotides were hybridized to each other and inserted into vectors according to the following process steps which are best illustrated in FIGS. 9a–9c:

The fragment A was digested with EcoRI and KpnI and ligated into EcoRI and KpnI cleaved pGem-3Z(+). The resulting plasmid was named pGA. The identity of the insert in pGA (as well as in all the subsequent intermediate plasmids created in the course of this work) was confirmed by sequencing.

Fragments $B_2$ and $B_3$ were ligated together and this ligation mixture was, together with fragment $B_1$, added to the SstII and SmaI digested and dephosphorylated plasmid pGA and incubated with the T4 DNA ligase in a buffer. This reaction mixture was transformed into an *E. coli* host and the resulting clones were screened for presence of the plasmid pGAB3.

Fragments $B_4$ and C were ligated together and the resulting fragment $B_4$-C was excised from an agarose gel after electrophoresis of the ligation mixture. This fragment was then ligated with the fragment $B_3$. This ligation mixture was again electrophoresed on an agarose gel and the $B_3$-$B_4$-C fragment was excised and ligated into BamHI and XmaIII digested pGAB3 to produce the plasmid pGAC.

Cloning of the wf8r coding sequence under control of the T7 derived regulatory elements The applicants chose as their expression vector the plasmid pGEMEX-2 which is available from the Promega Co. of Madison, Wis. Present in this plasmid is a fragment of the T7 bacteriophage gene 10 (T7g10), including its promoter, ribosome binding site and 260 codons specifying the N-terminal amino acids of the gene 10 product (P10). As shown in FIG. 9b, downstream from this fragment is a multiple cloning site followed by a T7 transcription terminator sequence. When the pGEMEX-2 is transformed into the E. coli JM109 (DE3), which harbors a chromosomal copy of the T7 RNA polymerase gene under control of the lacZ regulatory sequences, the P10 protein sequences will be transcribed by the T7 RNA polymerase upon induction by the isopropylthio-β-galactoside (IPTG) which is an inducer of the lacZ promoter. The T7 polymerase is very specific for the T7 promoters and will not transcribe any native E. coli genes. The protein 10 of the T7 phage is one of the most abundant proteins in the T7 infected cells due to high strength of its promoter and high efficiency of its ribosome binding site (see, Studier et al., J. Mol. Biol. 189:113–130 (1986) and Olins et al., Gene 73:227–235 (1988)). These features of the pGEMEX-2/JM109(DE3) vector/host combination have made it a promising system for high-efficiency expression of the wf8r gene. The applicants' objective, therefore, was to insert the wf8r structural sequences in frame downstream from the T7 gene 10 and express it as a P10:WF8R fusion protein.

FIG. 9b shows the EcoRI-BamHI fragment of pGAC, containing the wf8r structural sequences, was subcloned into pGEMEX-2 to create the plasmid pGGAC. The in-frame fusion to the T7 gene 10 was created by cleaving off the EcoRI-ClaI fragment of wf8r, filling the protruding ends and religating to produce the plasmid pX284.

To reduce the foreign (non-WF8R) amino acid content of the N-terminal end of the fusion protein, the pX284 was digested with KpnI and NheI. Both termini were blunt-ended by T4 DNA polymerase and the DNA was religated to produce the plasmid pX28. This procedure removed 257 codons from the P10 part of the fusion protein. Left in the resulting fusion protein were three N-terminal amino acids of the P10 followed by 24 amino acids coded by the multiple cloning site upstream from wf8r sequences.

Expression of the fusion proteins coded by the pX284 and pX28 plasmids

The pX28 and pX284 were transformed into JM109 (DE3). The proteins produced in either the JM109 (DE3) [pX28] or in the JM109 (DE3) [pX284] after induction by IPTG in mid- or late-logarithmic growth phase, have been analyzed by sodium dodecyl sulfate (SDS)—polyacrylamide gel electrophoresis (SDS-PAGE). No fusion protein (expected MW=10.5 kd) was detected from the strain bearing pX28 while a low-level expression of the fusion protein (MW=37.3 kd) was observed in the pX284 bearing strain. Studies of cell viability in these strains have shown that both strains are adversely affected with respect to growth and stability of the plasmid (these effects were more pronounced in the pX28 harboring strain). The applicants concluded that the WF8R must be toxic to the cells and that the cells were reacting to this toxicity by loss or mutation of the plasmid and by degradation of the proteins. To avert this problem the applicants decided to protect the fusion protein from intracellular degradation, as well as to protect the cells from the toxicity of WF8R, by adding to the fusion a C-terminal end derived from E. coli β-galactosidase.

Generation of the P10:WF8R:β-galactosidase fusion gene φ(T7g10:wf8r:lacZ)

The plasmid pMC1403 contains a fragment of the lac operon truncated at its 5'-end for all the regulatory sequences and the first seven codons of the lacZ gene (see, Casadaban et al., J. Bacteriol. 143:971–980 (1980)). The 8th codon of lacZ in this plasmid is attached at the BamHI site to a short multiple cloning cassette consisting of EcoRI, SmaI, and BamHI recognition sequences. To produce a translational fusion between the construct from pX28 and the lacZ fragment from pMC1403 the C part of the wf8r had to be modified to remove the two tandem termination codons present at its 3'-end (FIG. 8f). The applicants therefore substituted the C fragment of pX28 with the fragment CΔ1 (FIG. 8g). The CΔ1 has a point deletion at the end of the first termination codon. This mutation introduced a frame shift which added three new amino acid codons to the wf8r sequence and provided a potential for an in-frame read-through to the lacZ sequences upon ligation at the BamHI site. The resulting plasmid, pX28CΔ1, was digested with SmaI and BamHI and the released fragment, containing the entire fusion gene, including the regulatory sequences, was inserted into the SmaI and BamHI digested pMC1403, generating the plasmid pMX28L. Colonies of a lac⁻ E. coli strain transformed with pMX28L were colored when plated on agar substituted with chromogenic indicator of β-galactosidase activity. This result confirmed the in-frame nature of the fusion with lacZ, as well as the expression of the fusion protein. This result has also shown that the E. coli RNA polymerase recognizes the T7 promoter and can initiate a low-level transcription from this promoter (this result was later confirmed on an SDS-PAGE). To increase the level of expression of the P10:WF8R:β-gal fusion protein (pMC1403 is a lower copy number plasmid than pGEMEX-2 and the expression of the fusion protein in PMX28L have proven to interfere with the expression of the amp$^r$ gene) the applicants subcloned the SmaI-SalI fragment of the pMX28L into pGEMEX-2, creating the plasmid pGX28L (FIG. 9C).

Expression of the fusion protein (P10:WF8R:β-gal) in the JM109 (DE3) [pGX28L] cells One half hour after addition of IPTG to the growth media, the JM109 (DE3) [pGX28L] cells produce a protein of a higher apparent molecular weight (124 kd) then the β-galactosidase (116 kd). The double fusion protein was identified in gels with antibodies to the β-galactosidase portion. In the applicants initial attempts of expression only small amounts of this fusion protein were produced after 3-hr post-induction in complex media at 37° C. The applicants improved the yield of the protein dramatically (by 575%) by renewal of media at the time of induction. Further increase in yield (up to 630% of the initial value) was achieved by growing the induced cells at 25° C. overnight. At 37° C. the yield of the fusion protein did not increase significantly at growth times longer than 1-hr post induction. The improvement in yield was measured by comparing the protein bands on SDS-PAGE using as an internal control a band representing a prominent cellular protein of 70 kd apparent MW. The optimal yield of the fusion protein is 4.5–6.5 mg of the protein per gram of wet cell pellet, or 19–20 mg of fusion protein per liter of cell culture.

Purification of the fusion protein produced by the JM109 (DE3) [pGX28L] cells

The cells produce the fusion protein partially as insoluble aggregates and partially as soluble protein. Recently it was learned that the percentage of soluble protein that can be recovered from the cells depends both on the method of growth (42–45% soluble protein recovered from the cells grown at 25° C. vs 7–9% of soluble protein recovered from the 37° C. grown cells) as well as on the method of cell lysis (the insoluble aggregates of fusion protein can be solubilized by a pressure treatment in the French Pressure Cell). The fusion protein is purified as follows. The harvested cell pellet is resuspended in Tris hydrochloride (pH=8) and ethylenediaminetetraacetate (EDTA) containing buffer (TE), the cells are lysed in a French Pressure Cell (15000 psi) and the content of insoluble fusion protein in the cell extract is collected by centrifugation. The pellet is resuspended again in the TE buffer and pressure treated in the French Pressure Cell again and the resulting solution is then centrifuged.

The resulting pellet contains the rest of the aggregated fusion protein, which is essentially pure of most of the cellular proteins, except two (MW 20–30 kd) that always co-purify with this fraction. The supernatant from the second centrifugation is combined with the supernatant of the first centrifugation and the fusion protein content of this combined supernatant is precipitated with 10% ammonium sulfate. The precipitate, containing 80–90% of the total produced fusion protein constitutes the partially purified protein used for further manipulations.

Excision of the WF8R protein from the P10:WF8R:β-gal fusion protein

The WF8R is excised from the fusion protein by the enzyme Clostripain available from the Promega Co. of Madison, Wis. This enzyme digests proteins at the carboxylic site of arginine residues. As seen in FIGS. 8*f*, cleavage at the carboxylic site of arginine will leave the WF8R protein with a C-terminal arginine (end of first row of the C fragment). At the N-terminal end of the WF8R protein, the fusion with P10 has added an arginine residue three amino acid residues in front of the serine residue initiating the WF8R in the design of the wf8r gene (underlined in fragment A of FIG. 8*a*). Thus, the WF8R protein excised from the fusion protein by the Clostripain enzyme will have the following N-terminal amino acids: N-Asn-Ser-Met-Ser- (SEQ ID NO:43) where the underlined serine residue is the one underlined in FIG. 8*a* of fragment A.

The applicants are currently in the process of making a minor modification in the C fragment of the wf8r gene present in the pGS28L plasmid. This modification will make the N-terminal codons of the WF8R protein after digestion with Clostripain identical to the N-terminal codons of the native flounder AFP. The applicants are substituting the current EcoRI-SstII fragment with the DNA sequence (SEQ ID NO:39 and SEQ ID NO:40) and amino acid codon sequence (SEQ ID NO:41) shown in FIG. 10. The four codons which are different from the current version of the EcoRI-SstII fragment in the gene are underlined. In the new version of the gene the methionine codon will be substituted with an arginine codon and the following serine codon, which will thus encode the first amino acid of the WF8R protein released from the fusion with Clostripain cleavage, will become asparagine as in the native fish protein.

Purification of the WF8R protein

The WF8R protein excised by the Clostripain digestion from the fusion protein should be purified by reverse phase high-performance liquid chromatography (HPLC) and assayed for its antifreeze activity.

The plasmid is a PgX28L and is expressed in the bacterium JM109 (DE3). This bacterium is not suitable for long term maintenance of cultures. Therefore, a deposit has been made with the American Type Culture Collection (ATCC) of Rockville, Md., of the plasmid PgX28L in the *E.coli* strain DH5αand has ATCC number 68425.

While the invention has been described in terms of its preferred embodiments where a synthetic AFP longer than that which occurs in nature was biosynthetically produced in an *E.coli* host which had been modified with a synthetic gene having a particular coding sequence, those skilled in the art will recognize that the invention can be practiced with modification within the spirit and scope of the appended claims.

Having thus described our invention, what we claim as new and desire to secure by Letters Patent is as follows:

1. A protein having an amino acid sequence defined by blocks 1–6 of FIG. 4 (SEQ ID NO: 2).

2. A protein having an amino acid sequence defined by blocks 2–7 of FIG. 4 (SEQ ID NO: 2).

3. A protein having an amino acid sequence defined by blocks 3–8 of FIG. 4 (SEQ ID NO: 2).

4. A protein having an amino acid sequence defined by blocks 1–8 of FIG. 4 (SEQ ID NO: 2).

5. A protein as shown in FIG. 4 (SEQ ID NO: 2).

6. A protein as shown in FIG. 4 (SEQ ID NO: 2) expressed from the plasmid in ATCC deposit No. 68425.

* * * * *

SEQUENCE LISTING

```
(1) GENERAL INFORMATION:

(iii) NUMBER OF SEQUENCES: 43

(2) INFORMATION FOR SEQ ID NO:1:

(i) SEQUENCE CHARACTERISTICS:
          (A) LENGTH: 38 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:1:

Asp Thr Ala Ser Asp Ala Ala Ala Ala Ala Ala Leu Thr Ala Ala Asp
1               5                   10                  15

Ala Ala Ala Ala Ala Ala Leu Thr Ala Ala Asp Ala Ala Ala Ala Ala
            20                  25                  30

Ala Ala Thr Ala Ala Xaa
        35

(2) INFORMATION FOR SEQ ID NO:2:

(i) SEQUENCE CHARACTERISTICS:
          (A) LENGTH: 98 amino acids
```

(B) TYPE: amino acid
            (D) TOPOLOGY: linear (ii) MOLECULE TYPE: protein (xi) SEQUENCE DESCRIPTION: SEQ ID NO:2:

Met Ser Thr Ala Ser Asp Ala Ala Ala Ala Ala Ala Thr Ala Ala
 1               5                  10                  15

Thr Ala Ala Ala Ala Ala Ala Ala Thr Ala Ala Thr Ala Ala Ala
             20                  25                  30

Ala Ala Ala Thr Ala Ala Thr Ala Ala Ala Ala Ala Ala Thr Ala
             35                  40                  45

Ala Thr Ala Ala Ala Ala Ala Ala Thr Ala Ala Thr Ala Ala Ala
         50                  55                  60

Ala Ala Ala Ala Thr Ala Ala Thr Ala Ala Lys Ala Ala Leu Thr
     65                  70                  75                  80

Ala Ala Asn Ala Ala Ala Ala Ala Ala Thr Ala Ala Ala Ala Ala
                 85                  90                  95

Arg Gly (2) INFORMATION FOR SEQ ID NO:3:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 31..324

(xi) SEQUENCE DESCRIPTION: SEQ ID NO:3:

GAATTCGTAG ATCTGTAAGC AGGTTTATCG ATG TCC ACC GCT TCC GAC GCC GCG         54
                                Met Ser Thr Ala Ser Asp Ala Ala
                                 1               5

GCA GCA GCA GCT GCT ACT GCG GCG ACC GCA GCA GCG GCT GCG GCA GCT        102
Ala Ala Ala Ala Ala Thr Ala Ala Thr Ala Ala Ala Ala Ala Ala Ala
         10                  15                  20

ACT GCG GCG ACC GCA GCA GCG GCT GCG GCA GCT ACT GCG GCG ACC GCA        150
Thr Ala Ala Thr Ala Ala Ala Ala Ala Ala Ala Thr Ala Ala Thr Ala
     25                  30                  35                  40

GCA GCG GCT GCG GCA GCT ACC GCT GCT ACC GCA GCA GCT GCT GCG GCA        198
Ala Ala Ala Ala Ala Ala Thr Ala Ala Thr Ala Ala Ala Ala Ala Ala
                 45                  50                  55

GCA ACT GCG GCG ACC GCA GCA GCG GCT GCG GCA GCT ACC GCA GCT ACT        246
Ala Thr Ala Ala Thr Ala Ala Ala Ala Ala Ala Ala Thr Ala Ala Thr
             60                  65                  70

GCA GCT AAA GCT GCG GCT CTG ACT GCT GCA AAC GCA GCG GCT GCT GCG        294
Ala Ala Lys Ala Ala Ala Leu Thr Ala Ala Asn Ala Ala Ala Ala Ala
         75                  80                  85

GCG GCG ACT GCT GCG GCA GCG GCT CGT GGT TGATAAGGAT CC                   336
Ala Ala Thr Ala Ala Ala Ala Ala Arg Gly
     90                  95

(2) INFORMATION FOR SEQ ID NO:4:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:4:

```
GGATCCTTAT CAACCACGAG CCGCTGCCGC AGCAGTCGCC GCCGCAGCAG CCGCTGCGTT    60

TGCAGCAGTC AGAGCCGCAG CTTTAGCTGC AGTAGCTGCG GTAGCTGCCG CAGCCGCTGC   120

TGCGGTCGCC GCAGTTGCTG CCGCAGCAGC TGCTGCGGTA GCAGCGGTAG CTGCCGCAGC   180

CGCTGCTGCG GTCGCCGCAG TAGCTGCCGC AGCCGCTGCT GCGGTCGCCG CAGTAGCAGC   240

CGCAGCCGCT GCTGCGGTCG CCGCAGTAGC AGCTGCTGCT GCCGCGGCGT CGGAAGCGGT   300

GGACATCGAT AAACCTGCTT ACAGATCTAC GAATTC                             336
```

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Thr Ala Ala Thr Ala Ala Ala Ala Ala Ala Ala
 1               5                  10
```

(2) INFORMATION FOR SEQ ID NO:6:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Thr Ala Ser Asp Ala Ala Ala Ala Ala Ala Ala
 1               5                  10
```

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

```
Thr Ala Ala Thr Ala Ala Lys Ala Ala Ala Leu
 1               5                  10
```

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Thr Ala Ala Asn Ala Ala Ala Ala Ala Ala Ala
 1               5                  10
```

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:9:

```
GCTGCGGCCG CGGCAGCCAC CGCAGCAACT GCA                          33
```

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:10:

```
GTAGCTGCGG TGGCTGCCGC GGCCGCAGCT GCA                          33
```

(2) INFORMATION FOR SEQ ID NO:11:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Ala Ala Ala Ala Ala Ala Ala Thr Ala Ala Thr
 1               5                  10
```

(2) INFORMATION FOR SEQ ID NO:12:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:12:

```
GCTGCGGCCG CGGCAGCCAC CGCAGCAACT GCAGCTGCGG CCGCGGCAGC CACCGCAGCA    60

ACTGCA                                                               66
```

(2) INFORMATION FOR SEQ ID NO:13:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:13:

```
GTTGCTGCGG TGGCTGCCGC GGCCGCAGCT GCAGTAGCTG CGGTGGCTGC CGCGGCCGCA    60

GCTGCA                                                               66
```

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:14:

GCTGCGGCCG CGGCAGCCTG CGCAGCAACT GCA                33

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:15:

GTAGCTGCGC AGGCTGCCGC GGCCGCAGCT GCA                33

(2) INFORMATION FOR SEQ ID NO:16:

(i) SEQUENCE CHARACTERISTICS:
        (A) LENGTH: 67 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:16:

GTGTGAATTC GTAGATCTGT AAGGAGGTTT ATCGATGTCC ACCGCTTCCG ACGCCGCGGT    60

ACCGAGG                                                              67

(2) INFORMATION FOR SEQ ID NO:17:

(i) SEQUENCE CHARACTERISTICS:
        (A) LENGTH: 67 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:17:

CCTCGGTACC GCGGCGTCGG AAGCGGTGGA CATCGATAAA CCTCCTTACA GATCTACGAA    60

TTCACAC                                                              67

(2) INFORMATION FOR SEQ ID NO:18:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

Ala Gly Leu Ser Met Ser Thr Ala Ser Asp Ala Ala Ala Ala Ala
1               5                  10                 15

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:19:

GGCAGCAGCA GCTGCTACTG CTGCCACCG                                              29

(2) INFORMATION FOR SEQ ID NO:20:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:20:

TGGCAGCAGT AGCAGCTGCT GCTGCCGC                                               28

(2) INFORMATION FOR SEQ ID NO:21:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

Ala Ala Ala Ala Ala Thr Ala Ala Thr Ala
1               5                  10

(2) INFORMATION FOR SEQ ID NO:22:

(i) SEQUENCE CHARACTERISTICS:
        (A) LENGTH: 64 base pairs
        (B) TYPE: nucleic acid
        (C) STRANDEDNESS: double
        (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:22:

CAGCGGCGGC TGCGGCAGCT ACTGCGGCGA CCGCAGCAGC GGCTGCGGCA GCTACTGCGG           60

CGAC                                                                        64

(2) INFORMATION FOR SEQ ID NO:23:

(i) SEQUENCE CHARACTERISTICS:
        (A) LENGTH: 72 base pairs
        (B) TYPE: nucleic acid
        (C) STRANDEDNESS: double
        (D) TOPOLOGY: linear (ii) MOLECULE TYPE: other nucleic acid
         (A) DESCRIPTION: /desc = "synthetic DNA"

(xi) SEQUENCE DESCRIPTION: SEQ ID NO:23:

CGGCCGTCGC CGCAGTAGCT GCCGCAGCCG CTGCTGCGGT CGCCGCAGTA GCTGCCGCAG    60

CCGCCGCTGC GG    72

(2) INFORMATION FOR SEQ ID NO:24:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Ala Ala Ala Ala Ala Ala Thr Ala Ala Thr Ala Ala Ala Ala Ala Ala
1               5                   10                  15

Ala Thr Ala Ala Thr
            20

(2) INFORMATION FOR SEQ ID NO:25:

(i) SEQUENCE CHARACTERISTICS:
        (A) LENGTH: 62 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:25:

GGCCGCAGCG GCTGCGGCAG CTACCGCTGC TACCGCAGCA GCTGCTGCGG CAGCAACTGC    60

GG    62

(2) INFORMATION FOR SEQ ID NO:26:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:26:

CCGCAGTTGC TGCCGCAGCA GCTGCTGCGG TAGCAGCGGT AGCTGCCGCA GCCGCTG    57

(2) INFORMATION FOR SEQ ID NO:27:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

Ala Ala Ala Ala Ala Ala Ala Thr Ala Ala Thr Ala Ala Ala Ala Ala
1               5                   10                  15

Ala Ala Thr Ala
            20

(2) INFORMATION FOR SEQ ID NO:28:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:28:

```
CCACCGCAGC AGCGGCTGCG GCAGCTACCG CAGCTACTGC A                41
```

(2) INFORMATION FOR SEQ ID NO:29:

(i) SEQUENCE CHARACTERISTICS:
        (A) LENGTH: 37 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:29:

```
GTAGCTGCGG TAGCTGCCGC AGCCGCTGCT GCGGTGG                     37
```

(2) INFORMATION FOR SEQ ID NO:30:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

```
Ala Thr Ala Ala Ala Ala Ala Ala Ala Thr Ala Ala Thr Ala
1               5                   10
```

(2) INFORMATION FOR SEQ ID NO:31:

(i) SEQUENCE CHARACTERISTICS:
        (A) LENGTH: 82 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:31:

```
GCTAAAGCTG CGGCTCTGAC TGCTGCAAAC GCAGCGGCTG CTGCGGCGGC GACTGCTGCG    60

GCAGCGGCTC GTGGTTGATA AG                                             82
```

(2) INFORMATION FOR SEQ ID NO:32:

(i) SEQUENCE CHARACTERISTICS:
        (A) LENGTH: 90 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:32:

```
GATCCTTATC AACCACGAGC CGCTGCCGCA GCAGTCGCCG CCGCAGCAGC CGCTGCGTTT    60
```

```
GCAGCAGTCA GAGCCGCAGC TTTAGCTGCA                                            90
```

(2) INFORMATION FOR SEQ ID NO:33:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

```
Ala Lys Ala Ala Ala Leu Thr Ala Ala Asn Ala Ala Ala Ala Ala
1               5                   10                  15

Ala Thr Ala Ala Ala Ala Ala Arg Gly
            20                  25
```

(2) INFORMATION FOR SEQ ID NO:34:

(i) SEQUENCE CHARACTERISTICS:
        (A) LENGTH: 81 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:34:

```
GCTAAAGCTG CGGCTCTGAC TGCTGCAAAC GCAGCGGCTG CTGCGGCGGC GACTGCTGCG          60

GCAGCGGCTC GTGGTTGTAA G                                                   81
```

(2) INFORMATION FOR SEQ ID NO:35:

(i) SEQUENCE CHARACTERISTICS:
        (A) LENGTH: 89 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:35:

```
GATCCTTACA ACCACGAGCC GCTGCCGCAG CAGTCGCCGC CGCAGCAGCC GCTGCGTTTG          60

CAGCAGTCAG AGCCGCAGCT TTAGCTGCA                                           89
```

(2) INFORMATION FOR SEQ ID NO:36:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

```
Ala Lys Ala Ala Ala Leu Thr Ala Ala Asn Ala Ala Ala Ala Ala
1               5                   10                  15

Ala Thr Ala Ala Ala Ala Ala Arg Gly Cys Lys Asp
            20                  25
```

(2) INFORMATION FOR SEQ ID NO:37:

(i) SEQUENCE CHARACTERISTICS:
            (A) LENGTH: 35 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:37:

AATTCAGATC TGCGAGATAC CGCTTCCGAC GCCGC                        35

(2) INFORMATION FOR SEQ ID NO:38:

(i) SEQUENCE CHARACTERISTICS:
            (A) LENGTH: 29 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:38:

GGCGTCGGAA GCGGTATCTC GCAGATCTG                              29

(2) INFORMATION FOR SEQ ID NO:39:

(i) SEQUENCE CHARACTERISTICS:
            (A) LENGTH: 12 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:39:

Asn Ser Asp Leu Arg Asp Thr Ala Ser Asp Ala Ala
1               5                   10

(2) INFORMATION FOR SEQ ID NO:40:

(i) SEQUENCE CHARACTERISTICS:
            (A) LENGTH: 78 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:40:

GGCCAAGTCG GCCGAGCTCG GAATTCGTCG ACCTCGAGGG ATCCGGGCCC TCTAGATGCG    60

GCCGCATGCA TAAGCTTG                                          78

(2) INFORMATION FOR SEQ ID NO:41:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:41:

GAATTCCCGG GGATCCC                                           17

(2) INFORMATION FOR SEQ ID NO:42:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:42:

GGGATCCCCG GGAATTC                                                    17

(2) INFORMATION FOR SEQ ID NO:43:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

Asn Ser Met Ser